(12) United States Patent
Ma et al.

(10) Patent No.: US 10,388,028 B2
(45) Date of Patent: Aug. 20, 2019

(54) APPARATUS AND METHOD FOR MEASUREMENT OF TRANSPARENT CYLINDRICAL ARTICLES

(71) Applicant: HERAEUS QUARTZ NORTH AMERICA LLC, Buford, GA (US)

(72) Inventors: Qiulin Ma, Duluth, GA (US); Evan P. Green, Lawrenceville, GA (US); James E. Beavers, Jr., Flowery Branch, GA (US)

(73) Assignee: HERAEUS QUARTZ NORTH AMERICA LLC, Buford, GA (US)

( * ) Notice: Subject to any disclaimer, the term of this patent is extended or adjusted under 35 U.S.C. 154(b) by 45 days.

(21) Appl. No.: 15/310,605

(22) PCT Filed: Jun. 17, 2014

(86) PCT No.: PCT/US2014/042790
§ 371 (c)(1),
(2) Date: Nov. 11, 2016

(87) PCT Pub. No.: WO2015/195102
PCT Pub. Date: Dec. 23, 2015

(65) Prior Publication Data
US 2017/0084050 A1 Mar. 23, 2017

(51) Int. Cl.
*G06T 7/00* (2017.01)
*G06T 7/62* (2017.01)
(Continued)

(52) U.S. Cl.
CPC ............... *G06T 7/62* (2017.01); *C03B 37/02* (2013.01); *G01B 11/08* (2013.01); *G01N 21/896* (2013.01);
(Continued)

(58) Field of Classification Search
CPC ... C03B 37/027; C03B 37/032; C03B 37/029; C03B 37/0146; C03B 2205/40; C03B 2205/07
See application file for complete search history.

(56) References Cited

U.S. PATENT DOCUMENTS 3,982,816 A 9/1976 Watkins
4,067,651 A 1/1978 Watkins
(Continued)

FOREIGN PATENT DOCUMENTS

CN 1666100 9/2005
CN 101891380 11/2010
(Continued)

OTHER PUBLICATIONS

International Search Report and Written Opinion dated Feb. 19, 2015 by the European Patent Office for counterpart international patent application No. PCT/US2014/042790.
(Continued)

*Primary Examiner* — Clifford Hilaire
(74) *Attorney, Agent, or Firm* — Stradley Ronon Stevens & Young, LLP

(57) ABSTRACT

An apparatus and a method for measurement of transparent cylindrical articles during their manufacture in high temperature furnaces having openings for viewing the articles as they pass through the furnace. The cylindrical articles may, for example, be optical fiber preforms which have at least two layers of vitreous material and from which optical fibers are made. Measurement is accomplished using a digital camera with a sensing and digital recording device and a lens, and a processor programmed with an algorithm which analyzes the images recorded by the sensing and digital recording device by eliminating noise, identifying and locating the outer edges of the transparent cylindrical article and
(Continued)

calculating measurements of the article including the diameter and the axial center of the article.

22 Claims, 10 Drawing Sheets

(51) Int. Cl.

| | |
|---|---|
| *G01B 11/08* | (2006.01) |
| *G01M 11/00* | (2006.01) |
| *G06T 7/136* | (2017.01) |
| *G06T 7/194* | (2017.01) |
| *H04N 5/225* | (2006.01) |
| *G01N 21/896* | (2006.01) |
| *G01N 21/952* | (2006.01) |
| *G01N 21/958* | (2006.01) |
| *C03B 37/02* | (2006.01) |

(52) U.S. Cl.
CPC ......... *G01N 21/952* (2013.01); *G01N 21/958* (2013.01); *G06T 7/0004* (2013.01); *G06T 7/136* (2017.01); *G06T 7/194* (2017.01); *G01M 11/30* (2013.01); *G01M 11/37* (2013.01); *H04N 2005/2255* (2013.01)

(56) References Cited

U.S. PATENT DOCUMENTS

| | | | |
|---|---|---|---|
| 4,123,242 | A | 10/1978 | Imoto et al. |
| 4,280,827 | A | 7/1981 | Murphy et al. |
| 4,319,901 | A | 3/1982 | Pellegrin et al. |
| 4,331,463 | A | 5/1982 | Briere et al. |
| 4,523,938 | A | 6/1985 | Grego |
| 4,847,509 | A | 7/1989 | Millet et al. |
| 4,882,497 | A | 11/1989 | Inoue et al. |
| 5,264,909 | A | 11/1993 | Rochester |
| 5,352,395 | A * | 10/1994 | Kallenbach ........... C04B 35/584 264/673 |
| 5,355,209 | A | 10/1994 | Grosso |
| 5,443,610 | A | 8/1995 | Urruti |
| 5,551,967 | A | 9/1996 | Urruti |
| 5,837,334 | A | 11/1998 | Yokokawa et al. |
| 6,425,270 | B1 | 7/2002 | Suzuki et al. |
| 6,571,583 | B1 | 6/2003 | Maurin |
| 6,661,502 | B1 | 12/2003 | Jakobsen et al. |
| 6,791,678 | B2 | 9/2004 | Huang et al. |
| 6,816,243 | B2 | 11/2004 | Shurgalin et al. |
| 7,057,735 | B2 | 6/2006 | Jasapara |
| 7,089,765 | B2 | 8/2006 | Schaper et al. |
| 7,292,758 | B2 | 11/2007 | Bayindir et al. |
| 7,921,675 | B2 | 4/2011 | Bookbinder et al. |
| 2002/0101508 | A1* | 8/2002 | Pollack .............. G01N 21/8507 348/85 |
| 2002/0146202 | A1* | 10/2002 | Reed .................... A61B 5/0084 385/34 |
| 2003/0160974 | A1 | 8/2003 | Demeyere et al. |
| 2004/0042747 | A1* | 3/2004 | Kim .................... C03B 37/0253 385/123 |
| 2005/0069015 | A1 | 3/2005 | Bogdahn et al. |
| 2010/0236289 | A1* | 9/2010 | Nakanishi ............. C03B 23/043 65/60.1 |
| 2012/0114285 | A1* | 5/2012 | Fukuda ............... C03B 37/0253 385/33 |

FOREIGN PATENT DOCUMENTS

| | | |
|---|---|---|
| CN | 102374849 | 3/2012 |
| DE | 19536960 A1 | 3/1996 |
| EP | 0582405 A1 | 2/1994 |
| JP | S62-171932 | 7/1987 |
| JP | H06-211534 | 8/1994 |
| JP | H10-287441 | 10/1998 |
| JP | 2000-162152 | 6/2000 |
| JP | 2005-515399 | 5/2005 |
| JP | 2009-209016 A | 9/2009 |
| JP | 2012-121761 A | 6/2012 |
| WO | 01/33184 A1 | 5/2001 |
| WO | 2006/129494 A1 | 12/2006 |

OTHER PUBLICATIONS

Office Action (and English translation) dated Mar. 26, 2018 from counterpart Japanese Patent Application No. 2016-573891.
Office Action (and English translation) dated Jan. 3, 2019 from counterpart Chinese Patent Application No. 2014800799385.

* cited by examiner

APPARATUS AND METHOD FOR MEASUREMENT OF TRANSPARENT CYLINDRICAL ARTICLES

TECHNICAL FIELD

The present invention relates generally to an apparatus and method for measurement of transparent cylindrical articles during their manufacture. Such articles include, for example, optical fiber preforms which have at least two layers of vitreous material and from which optical fibers are made.

BACKGROUND

Optical fibers are waveguides that transmit light, with minimal scattering and attenuation, between two locations. Optical fibers, also sometimes called fiber optics, are well known and used for illumination, communications, information transfer, and sensors, for example. Optical fibers are typically flexible and very thin, i.e., on the order of less than the thickness of a human hair. They have a transparent core and one or more transparent cladding layers. The core and cladding layers are made of vitreous material, such as high quality glass (made from, e.g., silica, fluoride, phosphates, etc.) or even certain plastics. Moreover, the core material has a refractive index which is greater than the refractive index of the material in the surrounding cladding layer or layers. These conditions enable total internal reflection of light signals passing through the fiber, resulting in an efficient waveguide.

Optical fibers are generally manufactured by drawing the fiber from a heated preform using a fiber drawing tower. Such towers are typically vertically oriented and have a guide to hold and guide a preform, end first, into the top of the tower, as well as a high temperature furnace to heat the preform in a controlled manner, and apparatus to apply controlled tension to the leading end of the preform, whereby a fiber of molten material forms. The fiber is typically cooled and solidified as it is drawn from the preform to provide a fine continuous optical fiber.

The preforms are generally cylindrical or tubular in overall shape, with circular cross-sectional profiles, but may have other cross-section profiles (e.g., oval, elliptical, angular, etc.). Like the fibers which are drawn from them, preforms have an axial core of transparent vitreous material which is selected and formulated to provide the particular light transmitting properties needed, such as refractive index, attenuation, etc., according to its intended end uses. The preform core is completely surrounded and enclosed by at least one cladding layer which is also made of transparent vitreous material, but which has a lower refractive index than that of the core.

There are several techniques practiced for making optical preforms, most of which involve one or more types of chemical vapor deposition (CVD), including inside vapor deposition, outside vapor deposition and vapor axial deposition. All such techniques generally involve depositing one or more layers of soot material onto a substrate, followed by high temperature heating to vitrify the deposited soot materials into solid glass. The substrate may be a rod of material that can withstand the subsequent high temperature heating, or it may be a previously deposited layer of soot material, or a previously formed and vitrified rod or layer of glass, or even some combination of these. In some cases, the heating step which vitrifies the layered soot material may be performed immediately prior to, or concurrently, with heating of the vitrified preform and drawing of the fiber, so that formation of the preform and formation of the fiber are sequential and continuous.

CVD techniques may be combined with more recently developed processes, known as rod-in-tube (RIT) and rod-in-cylinder (RIC), for manufacturing optical preforms. RIT and RIC methods both start with a core glass rod and a glass jacket (either a tube or cylinder). The core glass rod has a core and a primary cladding layer, both of which are transparent, and the refractive index of the core is greater than that of the primary cladding layer. The glass jacket provides a second layer of glass cladding material, also sometimes referred to as "overcladding." The glass jacket may be a large outer diameter cylinder, or the cylinder may be drawn into a smaller outer diameter tube, both of which have an axial opening sized to receive the core glass rod. The core glass rod and glass jacket are produced separately and then assembled by insertion of the core rod into the tube or cylinder, followed by heating and solidification in a vertically-oriented jacketing apparatus similar to the fiber drawing tower, to form a solid vitreous preform. The preform is then be fed to a fiber drawing tower, where it is heated and the optical fiber drawn from the leading edge of the heated preform.

It is clear that careful control of the amounts of soot materials deposited during CVD methods, as well as control of the dimensions (inner diameter, outer diameter, length, etc.) of the core rod and the tube or cylinder jackets before and during vitrification, and the diameter and thickness of the final optical fiber and its layers, are all of critical importance to ultimately producing optical fibers having the desired properties and quality. Therefore, there are various known methods and apparatus for measuring the various properties of the components of the preform, the preform itself, and the optical fiber during different stages of the overall manufacture process.

For example, the diameter of optical preforms, whether made by CVD, RIT, RIC, or other methods, is typically measured after vitrification, but before beginning the drawing of optical fibers therefrom. One such method involves directing a laser or other radiation beam at a preform, where the laser or beam is at a right angle to the longitudinal axis of the preform and is reciprocated back and forth from one side of the preform to the other, linearly in a plane also oriented at a right angle to the longitudinal axis of the preform. The image produced by such methods is recorded and analyzed to produce and report at least the outer diameter of the preform, and sometimes also the diameters of the core and cladding layers, as well as other information. Often, the image is captured by an image sensor, such as a charge-coupled device ("CCD") image sensor, and recorded as a digital image for manipulation and interpretation by a processor. Laser scanning methods where the image sensor is located on the opposite side of the preform from the laser source and receives the shadow image produced as the laser shines through the preform are known as the shadow technique.

There are limitations to the shadow measurement of diameter measurement, some of which are imposed by features of the apparatus. For example, typically the furnace apparatus in which heating and vitrification of the preform occur has an opening which is sized and shaped, often as a long narrow rectangle or slit, to accommodate the reciprocating scanning laser passing through the opening to the preform. Preforms produced by the RIT method can be manufactured having outer diameters (OD) up to about 110 millimeters (mm), and that diameter could be accurately measured using telecentric laser scanning gauges and image sensors appropriately installed and operated proximate to the furnace apparatus. Of course, due to the nature of laser scanning technology, the rectangular window or slit must be a bit wider than the widest preform to be measured and, for a time this was possible. However, customer demand for larger diameter preforms led to the development of the RIC method for manufacturing preforms having diameters between about 135 and 150 (mm), and even larger, and limitations of the geometry and function of the apparatus and the laser scanner technology required development of a new way to measure larger diameter preforms and equipment for practicing such a method.

The present invention provides a novel apparatus and method for measuring the diameter of optical preforms, or other optically transparent cylindrical articles, during their manufacture. The novel apparatus includes use of a digital camera having a lens and a image receiver and recorder, in place of the previously employed laser scanning apparatus, while the method employs an algorithm developed to analyze the image received by the image sensor in a manner which eliminates noise and redundancy in the image to determine the preform diameter.

SUMMARY

The present invention provides an apparatus for measuring a transparent cylindrical article, such as its diameter, during its manufacture in a high temperature furnace. The high temperature furnace has a lateral opening through which the cylindrical article is visible. The apparatus includes: (A) a digital camera having a lens affixed thereto and a sensing and digital recording device; and (B) a digital processor programmed with an algorithm.

The lens receives an optical image of the cylindrical article through the opening of the furnace wall, and directs the optical image to the sensing and digital recording device of the camera which converts the optical image to a digital image and records the digital image. In an exemplary embodiment, the lens is a wide angle lens (e.g., for a full-frame 35 mm image sensor, a lens having a focal length of less than 35 mm). In other embodiments, the lens may be a normal or a long-focus lens. The sensing and digital recording device may be a charge-coupled device ("CCD") image sensor. Alternatively, the sensing and digital recording device may be a complementary metal-oxide-semiconductor (CMOS) image sensor. The digital processor and algorithm accesses and interprets the digital image from the image sensor, and determines and reports the measurement of the cylindrical article, such as its diameter.

In some embodiments, the transparent cylindrical article may be an optical fiber preform comprising two or more layers of vitreous material. Moreover, the preform may include a core layer having a refractive index and a cladding layer having a refractive index and surrounding the inner layer. The refractive index of the core layer is greater than the refractive index of the cladding layer.

In some embodiments, the camera may be enclosed in a fluid-tight, fluid-cooled housing having a portal, aligned with the opening of the furnace wall, for passage therethrough of the optical image of the cylindrical article.

The apparatus may further include a reflector, such as a mirror, for directing the optical image received through the opening of the furnace wall and portal of the fluid-cooled housing to the lens of the camera.

In some embodiments of the apparatus of the invention, the furnace is a jacketed fluid-cooled graphite furnace having an heated interior with upper and lower annular graphite contacts through which the cylindrical article passes while being heated, wherein the upper and lower contacts each have annular walls and are proximate opposite ends of the heated interior, at least a portion of the lateral opening, through which the cylindrical article is visible, passing through the annular wall of the upper annular graphite contact, and wherein the upper and lower contacts receive and conduct electric current therethrough for heating the interior of the graphite furnace with the cylindrical article therein.

Embodiments of the present invention may also include a methods for measuring the diameter of a transparent cylindrical article during its manufacture in a high temperature furnace having a lateral opening through which the cylindrical article is visible. More particularly, the method may include: (A) receiving an optical image of the cylindrical article emitted through the lateral opening using a camera having a lens affixed thereto; (B) directing the optical image to a sensing and digital recording device; (C) converting the optical image to a digital image, and recording the digital image, using the sensing and digital recording device; and (D) interpreting the digital image and determining the diameter of the cylindrical article using a processor programmed with an algorithm. The sensing and digital recording device may be housed in the camera or it may be a device separate from the camera. The transparent cylindrical article may be an optical preform.

In some embodiments, the algorithm of the processor may have the steps of: (1) cropping the digital image to produce a smaller cropped digital image; (2) producing a gradient filtered image from the cropped digital image; (3) performing multiple gradient line scans and sum them together to form a grey level gradient spectrum; (4) identifying peaks which represent true left- and right-side edges of the cylindrical article; (5) calculating the outer diameter of the cylindrical article by taking the absolute value of the difference between the values of the true left- and right-sided edge of the cylindrical article; and (6) reporting the outer diameter of the cylindrical article.

More particularly, (1) the digital image is cropped to remove surrounding dark space and the resulting smaller cropped digital image includes only a bright field of view which was visible through the lateral opening of the furnace. Next, (2) a gradient filtered image is produced from the cropped digital image using a standard deviation light filter.

The third step of the algorithm (3) requires performing multiple gradient line scans and sum them together to form a grey level gradient spectrum having multiple left-sided peaks, multiple right-sided peaks and multiple minor background peaks. The multiple gradient lines are scanned within a scan area proximate to a vertical center of the gradient filtered image and extending horizontally across the full width of the gradient filtered image.

For the fourth step of the algorithm (4), identifying which of the multiple left- and right-sided peaks in the grey level gradient spectrum represent true left- and right-side edges of the preform is accomplished as follows. On the grey level gradient spectrum, a left-sided peak window area is selected which encompasses the multiple left-sided peaks, and a right-sided peak window area is selected which encompasses the multiple right-sided peaks, leaving the minor background peaks outside each window area for separate analysis. Then, a baseline is established for peak detection which eliminates the minor background peaks from further analysis by: (i) dynamically sampling a portion of the minor background peaks and calculating a noise floor level based on said dynamic sampling; (ii) adding a predetermined threshold amount to the noise floor level to derive said baseline; and (iii) thereafter, ignoring any peaks below the established baseline. Thereafter, a target left-sided peak and a target right-sided peak are identified to provide numerical values for the positions of the true left- and right-sided edges of the preform, respectively, by: (i) analyzing each of the multiple left-sided peaks which are higher than said baseline in the left-sided peak window area, selecting the target left-sided peak which is positioned farthest to the left in the left-sided peak window area and recording its position as a numerical value equal to the true left-sided edge of the preform; (ii) analyzing each of the multiple right-sided peaks which are higher than said baseline in the right-sided peak window area, selecting the target right-sided peak which is positioned farthest to the right in the right-sided peak window area and recording its position as a numerical value equal to the true right-sided edge of the preform.

Finally, (5) the outer diameter of the cylindrical article is calculated by taking the absolute value of the difference between the values of the true left- and right-sided edge of the cylindrical article which were determined in the fourth step (4), and (6) the outer diameter of the cylindrical article is reported.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION

Figure 1:
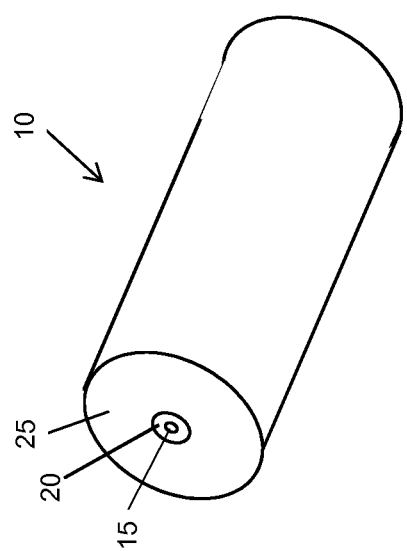
FIG. 1 is a schematic perspective view of an exemplary optical preform showing the core and cladding layers.

Embodiments of the present invention may include an apparatus and method for measuring a transparent cylindrical articles, such as optical fiber preforms, during their manufacture. For example, without limitation, the transparent cylindrical articles include optical fiber preforms from which optical fibers are produced using a process known as drawing. Such optical preforms have at least two layers of vitreous material, a core and a cladding layer, where the core has a higher refractive index than the cladding layer. The preforms may, in some embodiments, have one or more additional layers of cladding, such as an "overcladding layer," which is also made of transparent vitreous material. FIG. 1 provides a schematic perspective view of an exemplary optical preform 10 showing its possible layers including a core 15, a first cladding layer 20 and an overcladding layer 25, such as are sometimes manufactured using CVD, RIT and RIC technologies.

It should be understood that while the invention is described in detail hereinafter in the context of measuring the diameter of such optical preforms, its application is not limited to measurement of optical preform diameters. Rather, as will be recognized by persons having ordinary skill in the relevant art, the transparent cylindrical articles need not be optical preforms, but instead may be a transparent core rod having an outer diameter, or a transparent cylinder having outer and inner diameters, or another article that happens to be cylindrical or tube-like and transparent but which does not relate to the fiber optics field. It is foreseen and intended that all such modifications and applications are included in the invention described and claimed hereinafter. Additionally, based on the detailed description provided herein, it is believed that persons of ordinary skill in the relevant art will recognize and be capable of making alterations and modifications to the embodiments disclosed herein without departing from the spirit of the invention.

As used herein, the term "vitreous" has its usual meaning of describing material that is similar to (i.e., has the characteristics or appearance of) glass such as transparency, brittleness, hardness, glossiness, etc.

As used herein, the term "transparent" has its usual meaning of describing material that transmits light without appreciable scattering so that bodies positioned on the other side of the material from an observer are seen clearly. This does not require perfect or exact transmission of light, but means that light is allowed to pass through such material with little or no interruption or distortion so that objects on the other side can be seen and recognized.

In one general embodiment, the invention includes apparatus for measuring the diameter of a transparent cylindrical article during its manufacture in a high temperature furnace. The type of furnace is not particularly limited in connection with the practice of the apparatus and method of the invention described herein. It is noted that while the furnace described in connection with various embodiments of the invention is a jacketed fluid cooled furnace, other types of furnaces are suitable when used to manufacture, modify or process a transparent cylindrical article which needs measurement.

Figure 2:
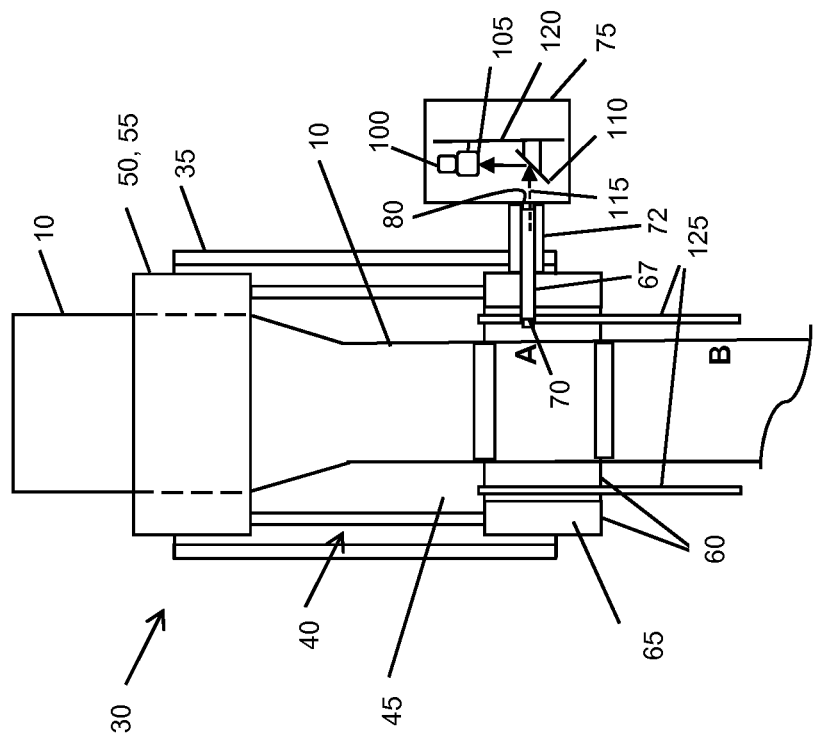
FIG. 2 is a schematic, partially cross-sectional, elevational front plan view of a high temperature furnace, a preform passing therethrough and an embodiment of the apparatus for measuring the preform diameter.

FIG. 2 provides a schematic elevational front view of a typical high temperature furnace 30 with an optical preform 10 passing therethrough. The furnace 30 shown in FIG. 2 is a jacketed fluid cooled furnace 30 having an outer jacket 35 which is shown in cross section to reveal the main heating region 40 having a heated interior 45 with upper and lower annular graphite contacts 50, 60 through which the cylindrical article, such as the optical preform 10, passes while being heated. The upper and lower contacts 50, 60 each have annular walls 55, 65 and are proximate opposite ends of the heated interior 45, as shown in FIG. 2. Furthermore, the furnace 30 has a protection tube 125 where the heated preform 10 begins to cool and solidify.

With reference still to FIG. 2, the furnace 30 has a lateral opening 70 through which the preform 10 inside the furnace 30 is visible to observers from the exterior environment. Accordingly, the lateral opening 70 is in communication with the heated interior 45 of the furnace 30, through which the preform 10 is passed during heating. Furthermore, the lateral opening 70 is at a vertical elevation where it is desired to measure the diameter of the preform 10, such as in the embodiment shown where heating of the preform 10 is substantially complete and just before or at the point at which the preform begins to cool. More particularly, the lateral opening 70 passes through an opening 67 in the annular wall 65 of the lower annular contact 60, through the wall of the jacket 35, and through a protective bridge 72, so that the lateral opening 70 is also in communication with the exterior environment.

Since the furnace 30 of this exemplary embodiment operates at high temperatures and is itself jacketed and fluid-cooled, a fluid-tight, fluid-cooled housing 75 is used to contain and protect a digital camera 100 and its lens 105. In an exemplary embodiment, the lens 105 is a wide angle lens (e.g., for a full-frame 35 mm image sensor, a lens having a focal length of less than 35 mm). In other embodiments, the lens 105 may be a normal or a long-focus lens. The housing 75 has a portal 80 and is affixed to the exterior of the furnace 30 such that the portal 80 is aligned with the lateral opening 70 so that the preform 10 is visible from within the housing 75.

Figure 3:
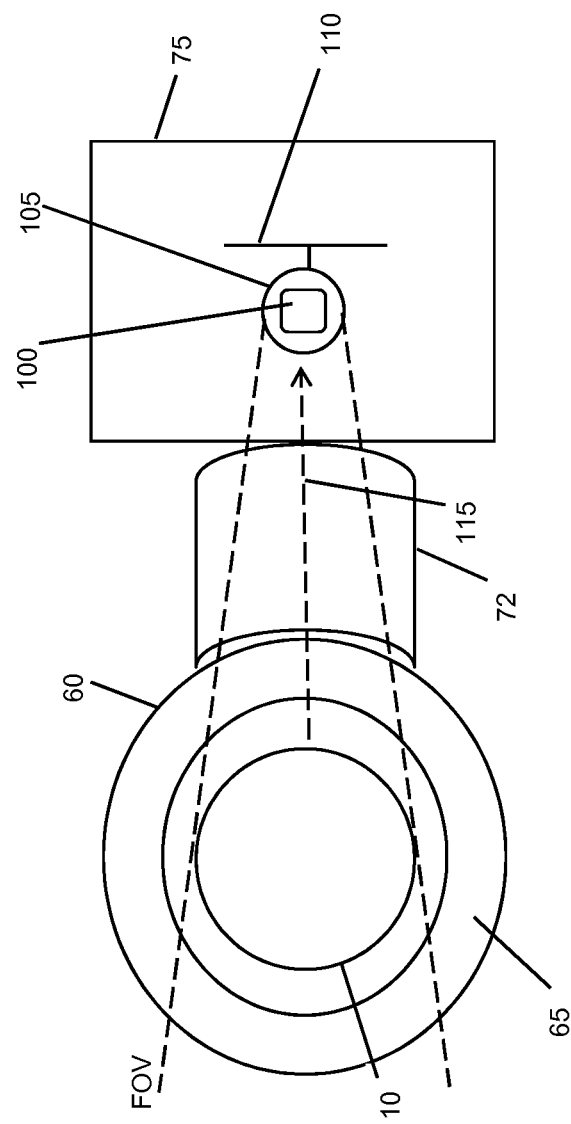
FIG. 3 shows a schematic top plan view of the furnace, preform and apparatus for measuring the preform diameter.

FIG. 3 shows a schematic top plan view of the apparatus for measuring the preform diameter including the camera 100, the lens 105 and the housing 75 which contains and protects the camera 100 and the lens 105. Also shown in FIG. 3 is the relative positioning of the lower contact 60 of the furnace 30 and the protective bridge 72 with the camera 100 and the lens 105, which enables a clear field of view (FOV, shown with a pair of dotted lines) between the lens 105 and the preform 10 inside the furnace 30 and passing through the lower contact 60. The mirror 110 is not visible since it lies beneath the camera 100 and the lens 105 in this top plan view.

It is noted that the upper and lower contacts 50, 60 receive and conduct electric current therethrough for heating the interior 45 of the furnace 30 with the preform 10 therein. The fact that the contacts 50, 60 conduct electricity and are part of the heating mechanism for the furnace 30 means that there are structural and functional limitations to the size (i.e., height and width) of the opening in the wall of the lower contact 60.

To obtain a wider field of view (e.g., see FOV in FIG. 3) for more reliable measurements, as well as larger preform OD measurements, widening of the opening through the lower contact 60 was investigated using a numerical model to predict the effects of a wider opening on the uniformity of heating in the heating region 40 of the furnace 30. The numerical model and its results are provided hereinbelow in the examples and shown in FIGS. 4A, 4B and 4C. An exemplary numerical model that may be used to determine the width of the opening is the Finite Element Method (FEM), though other numerical models are also contemplated. Based on the numerical modeling, it was determined that the opening could safely be widened to about 150 mm for the particular embodiment disclosed herein. In other embodiments, the maximum width of the opening may be less than or greater than about 150 mm. A person of ordinary skill in the art will understand based on this disclosure how to determine the maximum width of the opening by numerical modeling.

Referring again to FIGS. 2 and 3, the apparatus for measuring the diameter of a transparent cylindrical article during its manufacture includes: (A) the digital camera 100 having the lens 105 affixed thereto and a sensing and digital recording device, such as, for example, a charge-coupled device ("CCD") image sensor (inside camera, not shown); and (B) a digital processor (not shown per se) programmed with an algorithm. In other embodiments, the sensing and digital recording device may be a complementary metal-oxide-semiconductor (CMOS) image sensor. More particularly, the camera 100 and the lens 105 are positioned to enable the lens 105 to receive an optical image of the preform 10 article through the lateral opening 70. The lens 105 directs the optical image to the image sensor which converts the optical image to a digital image and records a digital image of the preform 10.

The apparatus may further comprising a reflector, such as a mirror 110 positioned intermediate the lateral opening 70 of the furnace 30 and the lens 105 of the camera 100. The reflector directs the optical image (see arrows 115 in FIG. 2), which is received through the lateral opening 70 of the furnace 30 and portal 80 of the housing 75, to the lens 105 of the camera 100. The lens 105 and the mirror 110 may be affixed to a mounting bar 120 within the housing 75, as shown schematically in FIG. 2.

In addition to the digital camera 100, the apparatus also includes a digital processor programmed with an algorithm which accesses and interprets the digital image from the image sensor, and determines and reports the diameter of the cylindrical article. Suitable processors and algorithms include those known now and in the future capable of analyzing digital images. Exemplary processors and algorithms are described in further detail hereinbelow in connection with the method of the invention.

It may be desirable to take a second measurement of the preform 10 after it has cooled and set, such as at the position in the furnace 30 where the preform 10 is emerging from the protection tube 125, e.g., at location B in FIG. 2. While the specific features are not shown in FIG. 2, when second preform measurement is to be taken at location B, the furnace 30 will have another lateral opening at location B, to enable viewing of the cooling preform exiting the protective tube 125 from the external environment, as well as a second apparatus for measuring the cooling preform 10 at location B, including another camera having its own sensing and digital recording device and lens, and another fluid-cooled housing. All such features may be the same as described above in connection with the main measurement location, i.e., location A, where the preform 10 is passing through the lower contact 60 of the furnace 30.

In another general embodiment, the invention provides a method for measuring the diameter of a transparent cylindrical article during its manufacture in a high temperature furnace having a lateral opening through which the cylindrical article is visible. The method includes the basic steps of: (A) receiving an optical image of the cylindrical article emitted through the lateral opening using a camera having a lens affixed thereto; (B) directing the optical image to a sensing and digital recording device; (C) converting the optical image to a digital image, and recording the digital image, using the sensing and digital recording device; and (D) interpreting the digital image and determining the diameter of the cylindrical article using a processor programmed with an algorithm.

With reference briefly back to the apparatus shown in FIGS. 2 and 3, an optical image 115 of the cylindrical article (e.g., preform 10) emitted through the lateral opening 70 of the furnace 30 is received by the camera 100 and the lens 105. Inside the camera 100, with the lens 105 properly mounted and adjusted, as will be readily understood by persons of ordinary skill in the art, the optical image 115 is directed to a sensing and digital recording device, also inside the camera (not shown), which then converts the optical image to a digital image, which is recorded. A processor programmed with an algorithm (not shown), which may be part of the camera 100, or may be a separate microprocessor, or part of a computer, etc., interprets the digital image to determine the diameter of cylindrical article (preform 10), as well as other properties, including but not limited to the position of the center of the cylindrical article (preform 10) and the existence and location of any joints in the core rod 15 (see FIG. 1) of a preform 10.

The last step (D) of interpreting the digital image and determining the diameter of the cylindrical article requires use of a processor programmed with an algorithm. The processor may, for example, without limitation, a computer, a computer component integrated with process control equipment and systems, a stand-alone microprocessor, or any other programmable processor known now or in the future to persons of ordinary skill that is capable of performing the algorithm, which will now be described in detail.

Generally, the algorithm includes the steps of: (1) cropping the digital image to produce a smaller cropped digital image; (2) producing a gradient filtered image from the cropped digital image; (3) performing multiple gradient line scans and sum them together to form a grey level gradient spectrum; (4) identifying which of multiple peaks in the grey level gradient spectrum represent the true left- and right-side edges of the preform; (5) calculating the outer diameter of the preform using the values of the true left- and right-side edges of the preform; and (6) reporting the outer diameter of the preform. Each of these steps will now be described in further detail. Sample images and spectra resulting from steps (1) to (4) of the algorithm are provided in FIG. 5.

Figures 5, 6:
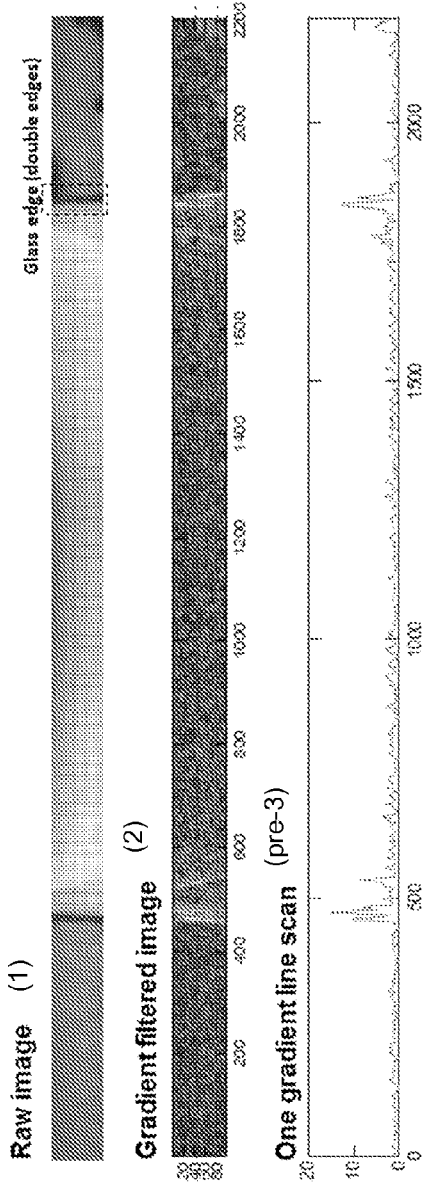
FIG. 5 shows the graphic data product of the first three steps of the algorithm used to process the optical image received by the camera.
FIG. 6 shows the approximate position of a scan window within which lines are selected for grey scale scanning in the third step of the algorithm.

In the first step of the algorithm, the digital image is cropped to remove surrounding dark space and produce a smaller cropped digital image (see "Raw image" (1) in FIG. 5). The smaller cropped image (1) includes only the bright field of view visible through the lateral opening of the furnace.

In the second step of the algorithm, a gradient filtered image (2) (see "Gradient filtered image" (2) in FIG. 5) is produced by applying a standard deviation filter to the cropped digital image (1). The standard deviation filter operates by creating the gradient filtered image (2) where each pixel of the gradient filtered image (2) is equal to a standard deviation of the pixels within a surrounding area of the corresponding pixel of the cropped digital image (1). Because the standard deviation of a pixel of the cropped digital image (1) will be highest where the surrounding area shifts from light to dark, or vice versa, the gradient filtered image (2) is used to detect edges in the cropped digital image (1).

In the third step of the algorithm, multiple line scans of the gradient filtered image (2) are collected and summed together to form a grey level gradient spectrum (see "grey level gradient spectrum" (3) in FIG. 5). While in some embodiments only one line scan may be collected, the grey level gradient spectrum (3) may have an improved signal-to-noise ratio when including the sum of multiple line scans.

In an exemplary embodiment, the grey level gradient spectrum (3) includes the sum of about 40 to 50 line scans. In other embodiments, the grey level gradient spectrum (3) may include more than 50 or less than 40 line scans. More particularly, the multiple gradient lines are scanned within a scan area proximate to a vertical center of the gradient filtered image (2) and extending horizontally across at least a portion of the full width of the gradient filtered image, i.e., sufficiently to encompass the entire width of the preform being measured (see white line 140 within the raw image of FIG. 6 to see approximate position of the scan area). Each line scan is performed by selecting a horizontal scan line position within the scan area of the gradient filtered image (2) and recording the grey level of the image along the set horizontal scan line position (see, e.g., "One gradient scan line" (pre-3) in FIG. 5). After collecting and summing the line scans of the gradient filtered image (2), the grey level gradient spectrum image (3) has multiple left-sided peaks 145, multiple right-sided peaks 150 and multiple minor background peaks 155a, 155b, 155c (again, see spectrum (3) in FIG. 5). In some embodiments, the grey level gradient spectrum image (3) may have only one left-sided peak, only one right-sided peak, and/or one or no minor background peaks. The left- and right-sided peaks 145, 150 contain the true left-sided and right-sided edges of the preform among them, respectively. The minor background peaks 155a, 155b, 155c represent noise resulting from the complex light background as well as the surface condition of the background graphite elements. By "minor" it is meant that these background peaks 155a, 155b, 155c are generally shorter or small than the left- and right-sided peaks of interest and need not be considered when measuring the preform diameter.

Figure 7:
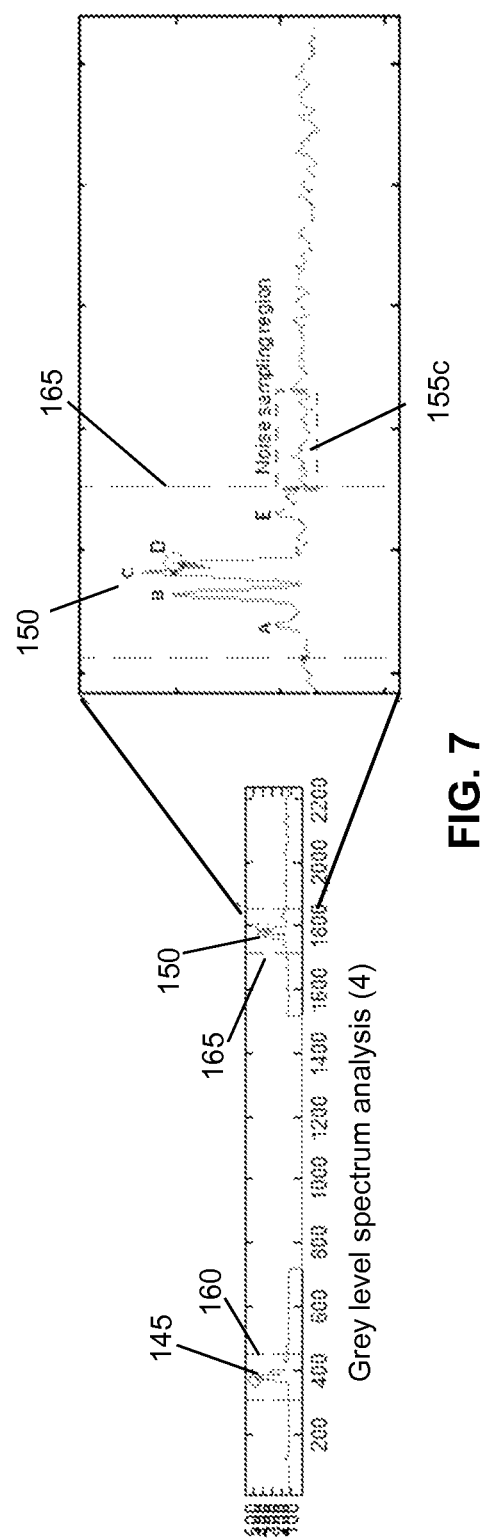
FIG. 7 shows the grey level gradient spectrum and details of its analysis during the fourth step of the algorithm.

In the fourth step of the algorithm, the true left- and right-side edges of the preform are identified from among the multiple left-sided and right-sided peaks 145, 150 in the grey level gradient spectrum (3). Referring now to FIG. 7, a grey level gradient spectrum analysis (4) is performed by selecting a left-sided peak window area 160 on the grey level gradient spectrum which encompasses the multiple left-sided peaks 145. Similarly, a right-sided peak window area 165 is also selected on the grey level gradient spectrum which encompasses the multiple right-sided peaks 150. These selections leave the minor background peaks 155a, 155b, 155c outside each window area unselected and are the subject of separate analysis as described below. It is noted that the left-sided peak window area 160 should be centered on the highest one of the multiple left-sided peaks 145, and likewise, the right-sided peak window area 165 should be centered on the highest one of the multiple right-sided peaks 150.

Identification of the true left- and right-side edges of the preform from the grey level gradient spectrum (4) (step (4), FIG. 7) further includes establishing a baseline for peak detection to eliminate the minor background peaks from further analysis. This is accomplished by, first, dynamically sampling a portion of the minor background peaks 155c and calculating a noise floor level based on the results of the dynamic sampling. The baseline is then derived by adding a predetermined threshold amount to the noise floor level. Thereafter, any peaks below the baseline are ignored for processing and analysis purposes. The threshold amount is determined by subtracting the noise floor level from the maximum peak height of the window selected of the grey level gradient spectrum (4), and then dividing the resulting height by a predetermined factor, where the factor is great enough to eliminate an identified noise peak such as peak E of FIG. 7, but not eliminate potential true edge peaks such as peak D of FIG. 7. In an exemplary embodiment, the factor may be about 3. In an alternative embodiment, the predetermined threshold amount may be determined by, for example, calculating 0.5 times the average height of the portion of minor background peaks dynamically sampled.

After eliminating the minor background peaks (noise and scatter data) from further consideration by the algorithm, numerical values for the positions of the true left- and right-sided edges of the preform, respectively, are obtained. First the target left-sided peak and the target right-sided peak are each identified. With reference now to FIG. 7, the multiple right-sided peaks 150 (all of which are higher than the baseline) in the right-sided peak window area 165 are analyzed and the peak which is positioned farthest to the right (peak D) in the right-sided peak window area 165 is selected to be the target right-sided peak. The position of the target right-sided peak is recorded as a numerical value equal to the true right-sided edge of the preform. While not shown per se, the same analysis and selection procedure is applied to the multiple left-sided peaks 145 (all of which are also higher than the baseline) in the left-sided peak window area 160, and the position of the target left-sided peak is recorded as a numerical value equal to the true left-sided edge of the preform. With reference still to FIG. 7, by the foregoing analytical procedure, the minor background peaks 155a, 155b, 155c can be ruled out in the window areas 160, 165. For the grey level gradient spectrum analysis (4) shown in FIG. 7, peaks A and E are ruled out by the baseline, while peaks B, C and D are left as peak candidates. Then peak D is identified as the target right-sided peak by its location at the right-most position in the right-sided peak window area 165.

Finally, the outer diameter (OD) of the preform is calculated by finding the difference between the values of the true left-sided edge and the right-sided edge of the preform, and then taking the absolute value of that difference. The OD of the preform may then be reported, or be the subject of further analysis and decision-making.

It is possible and may be desirable, after the optical image is acquired and converted to a digital image by the sensing and digital recording device, to perform a check to be sure the furnace is in operation before continuing with the remaining steps of the algorithm. For example, optionally, the average grey level in the cropped digital image may be calculated by the processor, and if it is below a predetermined threshold value, cease running the algorithm. The predetermined threshold value is selected based on the grey scale in use and should be a value low enough that persons of ordinary skill believe that when the average grey level in the cropped digital image is equal to or less than the threshold value it is reasonable to assume that the furnace is not in operation. More particularly, the predetermined threshold value may be determined by collecting an image of the oven from the camera while confirmed to not be in operation and determining the mean gray level of all the pixels of the image. In am exemplary embodiment where the image is a 8-bit grayscale image (i.e., 256 shades of gray) the mean gray level of the oven while not in operation may be 8 or below. The predetermined threshold value will vary from embodiment to embodiment based on oven design and the particular application.

In some embodiments, as the preform OD grows and reaches certain size, a mask (not shown) is applied in the center region of the preform to avoid interface defects/bubbles confusing the peak locking. The mask may be to be activated once the preform passes the start-up dripping phase, after which the preform OD does not change size quickly anymore. So, the left and right edges are being tracked for its last 20 locations, respectively. The (max−min) of the locations are calculated for each side of the edge. If the (max−min) of the locations is less than certain threshold for both glass edges, it means that the glass OD has reached sufficient stability. Therefore, the mask indicator is updated from 0 to 1. Starting from the next loop, once the program sees the indicator=1, it will open this mask and only scan the image horizontal gradient for the regions outside the mask. However, at the end phase of the draw, the preform OD becomes small again. Therefore, at that point, the mask should be disabled. The disabling point may be determined by seeing that the mask indicator=1 and preform OD is less than certain threshold.

Once the two glass edges are identified for OD calculation, another useful info that can be immediately derived is the preform center location. Its calculation formula is simply:

Preform center location=Location of left-handed edge+OD/2.

This information can be very helpful for the szug operator to improve preform bow. Once they see the center location oscillation amplitude passes a certain threshold, they would start to use "bow-bar" to dampen the center location oscillation and therefore correct potential bow formation to the preform.

Figure 8:
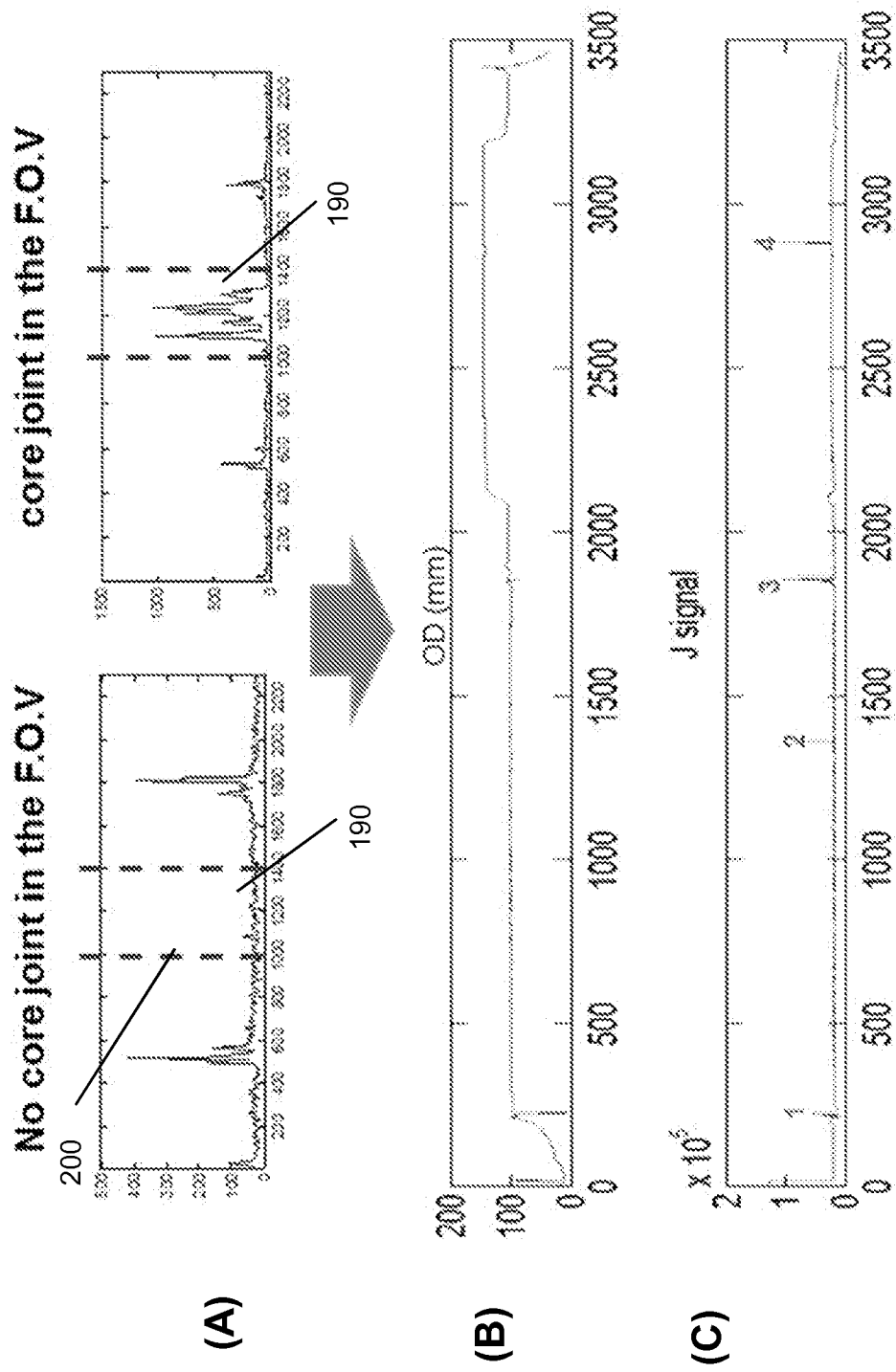
FIG. 8 shows sample graphic data relating to an algorithm for detection and measurement of a joint in the core of an optical preform.
Figure 9:
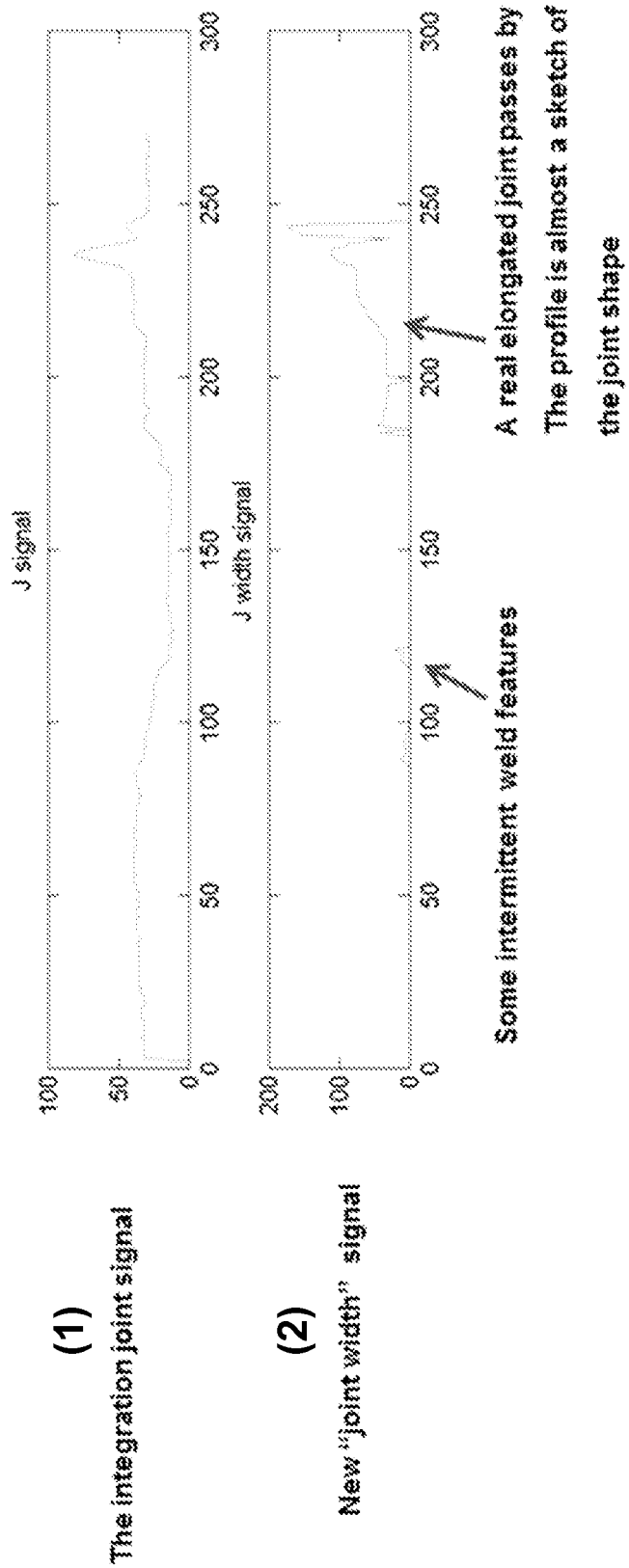
FIG. 9 shows comparative graphic data for simple and advanced algorithms for detection and measurement of a joint in the core of an optical preform.
Figure 10:
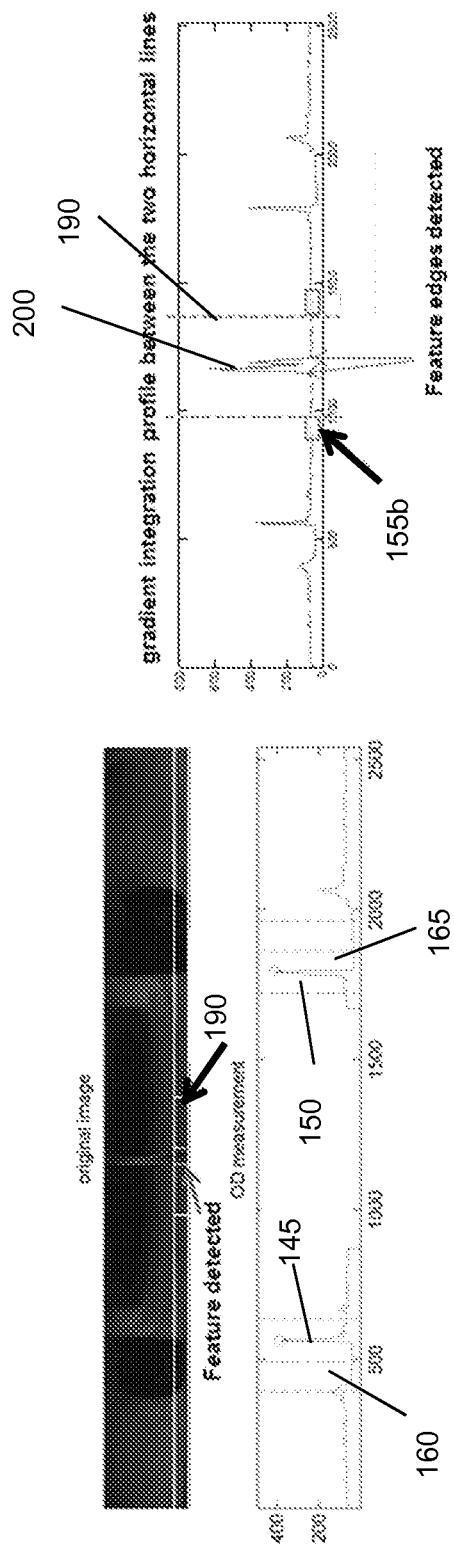
FIG. 10 shows a grey level gradient spectrum and details of its analysis for detection and measurement of a joint in the core of an optical preform.

FIGS. 8, 9 and 10 are provided to facilitate description of algorithms for common core joint detection using the above-discussed apparatus and digital images. With the digital camera image produced by the camera 100, a joint between core rods, or even the leading end of a first core rod, can be identified online using the method and apparatus of the invention. Such joint identification involves a first step, after production of the grey level gradient spectrum (see FIG. 5(3) and FIG. 8(A)), of determining whether there exist multiple intermediate peaks 185 located intermediate the multiple left- and right-sided peaks 145, 150 in the grey level gradient spectrum (A), by (a) selecting a central window area 190 intermediate multiple the left- and right-sided peaks 145, 150 (FIG. 5(3)), (b) calculating an area of integration for that central window area 190 and (c) analyzing the area of integration to determine if a joint is present. The area of integration may be analyzed by visual inspection by the operator, who subjectively identify when the area of integration has a sufficient value to indicate a joint. In other embodiments, the area of integration may be automatically analyzed to determine when the area of integration exceeds a predetermined value, which may vary from one application to another. When the area of integration exceeds the integration threshold value, a clear joint signal J is present, see FIGS. 8 (B) and (C), which can then be analyzed as described above in connection with the multiple left- and right-sided peaks to determine the size of the joint in the core rod.

Detection of the first core joint may be of significant importance to start-up control of the preform manufacture process. However, the first core joint is often interfered with by weld features (see FIG. 9) producing distracting weld peaks 195 in the grey level gradient spectrum. Such weld peaks 195 representing the first core joint may be more elongated compared with subsequent joints in the core rod. Therefore, a more sophisticated algorithm that captures the first core joint better has also been developed. FIG. 9 provides a comparison of this new "J width signal" (2) with the "J signal" (1) as described above.

For example, once it is determined that a joint exists in the preform 10, the grey level gradient spectrum is analyzed to determine the size and location of the joint. Similarly to the above-described method for determining the true left- and right-side edges of the preform (algorithm step (4)), as shown in FIG. 10, a central area window 190 is selected intermediate multiple the left- and right-sided peaks 145, 150, in the grey level gradient spectrum. Central area window 190 encompasses the multiple intermediate peaks 200 which represent the location of the joint, including the joint's left and right edges (not shown per se). Next a baseline for peak detection is established to eliminate minor background peaks from further analysis, as described above for algorithm step (4). Then, numerical values for the positions of the true left- and right-sided edges of the joint, respectively, are may be obtained. The outermost left- and right-sided peaks are each identified from among the multiple intermediate peaks 200 in the central window area 190 and their values are assigned as the locations of the true left- and right-sided edges of the joint, respectively. Joint width may then be calculated, as above for the width (diameter) of the preform, by finding the difference between the values of the true left and right edges of the joint. The joint width may then be reported, or be the subject of further analysis and decision-making. Furthermore, the location of the center of the joint may be determined using the following formula:

Location of joint center=Location of left edge of joint+(joint width)/2.

Additionally, a verification step may be performed before reporting values relating to an assumed core joint, where if the location of the joint center is too far (a thresh-holding) away from the preform center, it will be assumed that the feature detected is not actually a core joint and no positions for edges or width of the feature will be reported.

The invention and its various embodiments described above will be better understood with reference to the following examples, which are merely particular embodiments of the invention in practice and in no way limit the scope of the apparatus or method of the invention.

Examples

Determination of Widest Opening in Lower Contact that is Acceptable

Figure 4A:
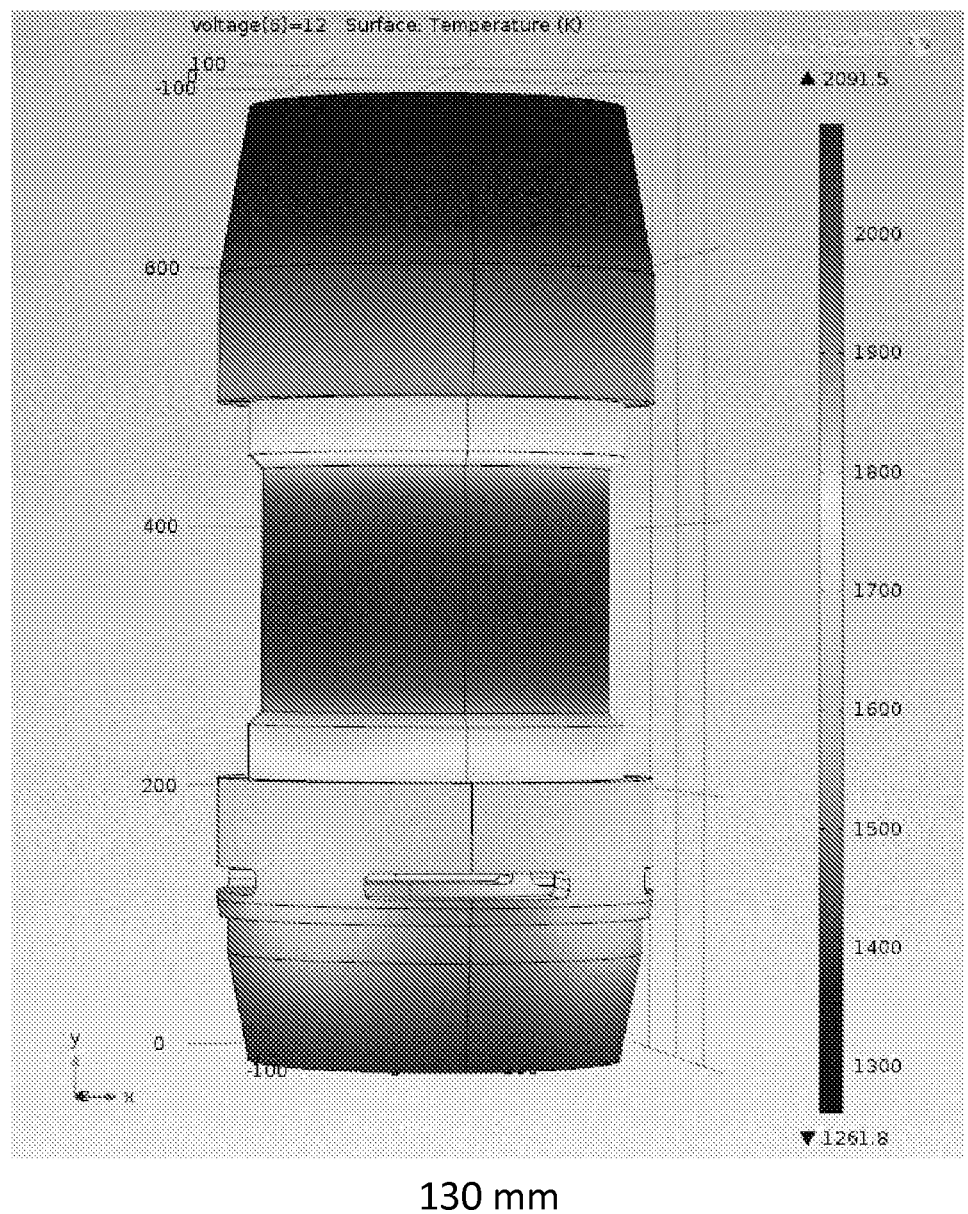
FIGS. 4A, 4B and 4C show the results of modeling the temperature pattern in the heated region of the furnace where the lower contact has an opening of varied width.
Figure 4B:
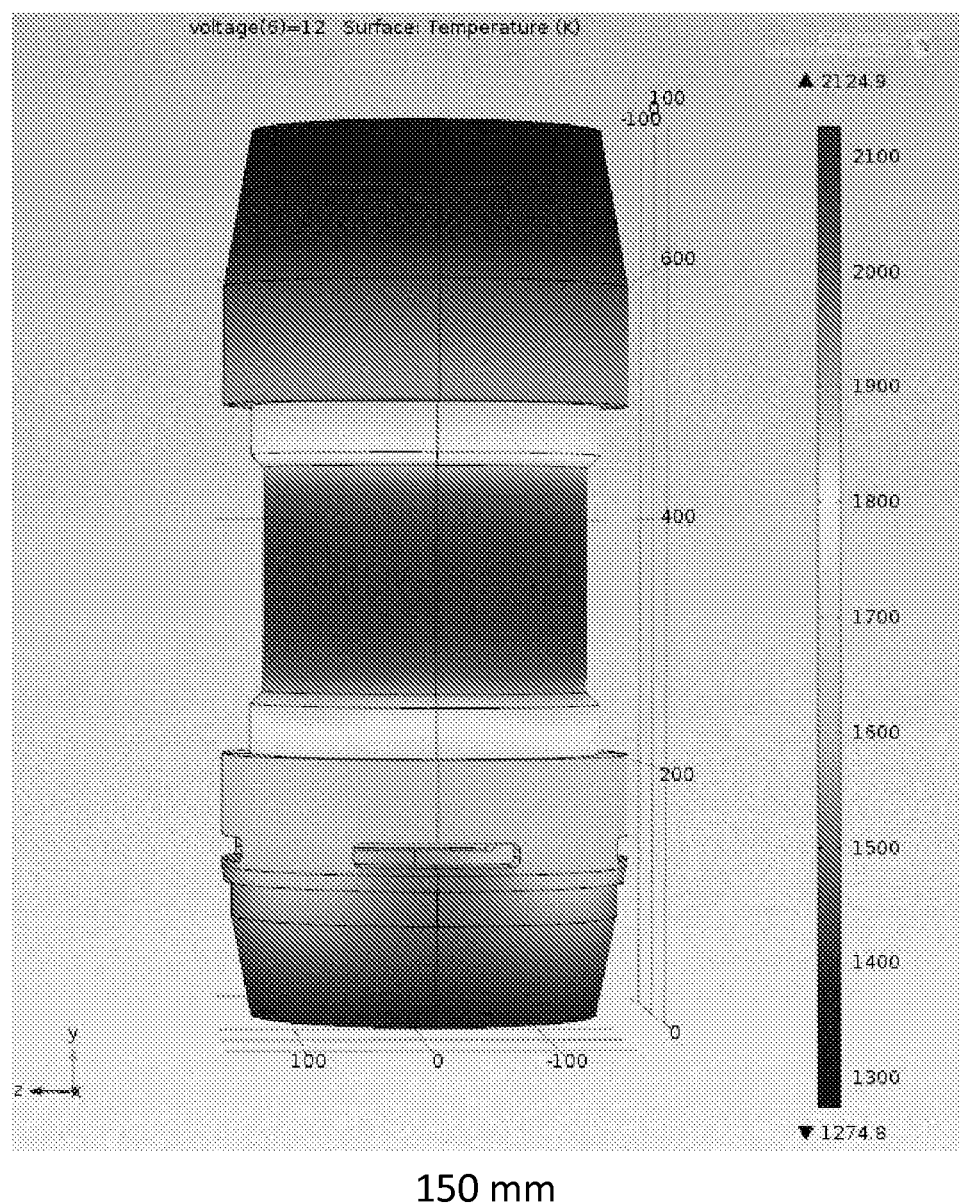
Figure 4C:
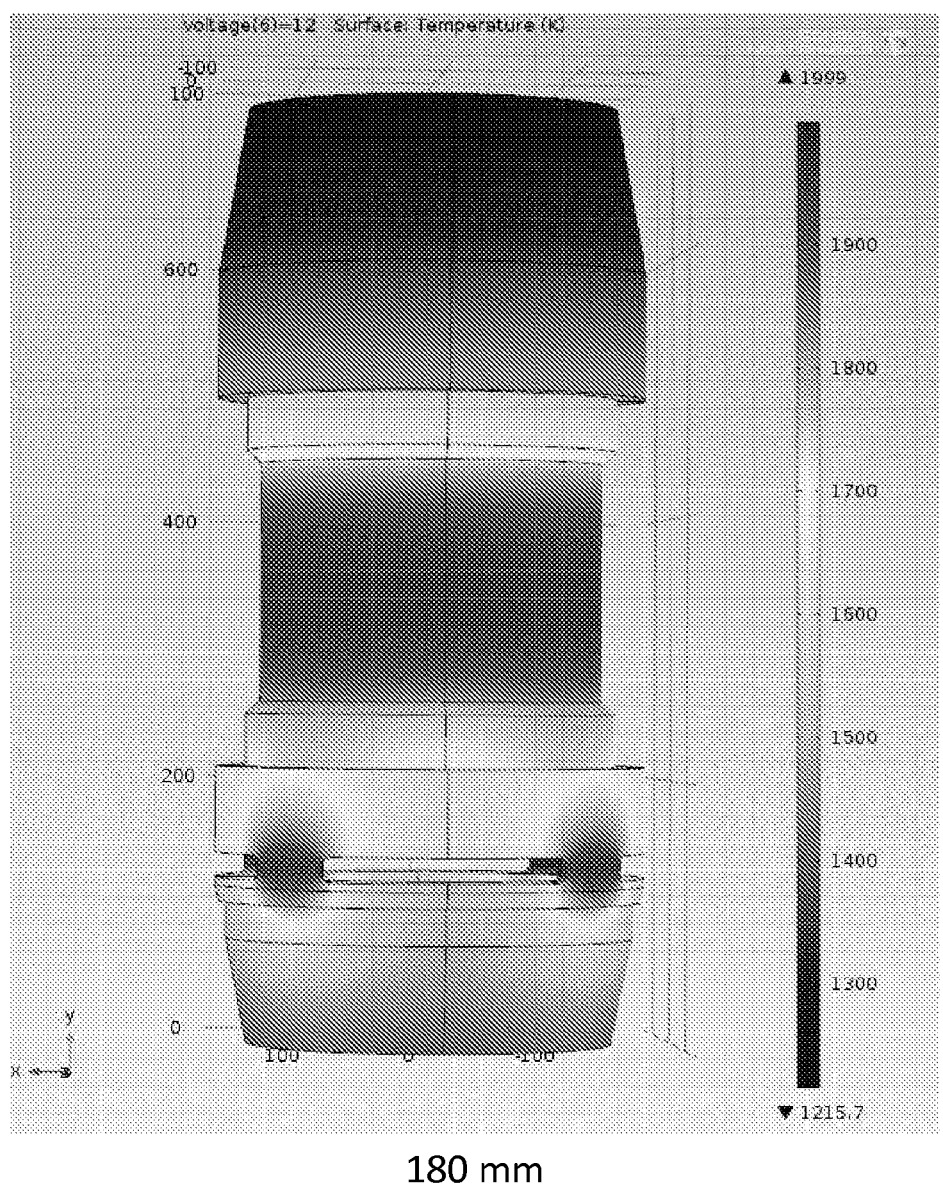

The opening through the wall 65 of the lower contact 60 was initially 130 mm. That width was sufficient for the previously used telecentric laser scanning method, but not for measuring preforms having diameters greater than about 130 mm. A numerical model was used to estimate the width at which a widened opening would cause unacceptable impacts on furnace temperature and uniformity throughout the heating region 40. The graphic results of the numerical modeling, which displayed the heating patterns achieved within the heating region 40 are is provided in FIGS. 4A, 4B and 4C. More specifically, FIG. 4A shows an acceptably uniform heating pattern with the original opening 67 of 130 mm. FIG. 4B also shows that an opening 67 widened to 150 mm still produces a heating pattern that is uniform and acceptable. When the opening 67 is widened to 180 mm, however, the numerical model predicted that the heating region 40 would be heated unevenly to an unacceptable degree, as shown in FIG. 4C.

Performance of Apparatus and Algorithm

Camera Equipment Used: "Guppy" 5 megapixel (MP) camera from Allied Vision Technologies, Modell F-503B.

Software: Allied Vision Technologies standard Firepackage v 3.1 was used to capture images from the camera. It is noted that other commercial, or even custom, programs may be used for this function.

Lenses: 16 mm fixed focal length MP lens from Edmund Optics. The focal length used depended on the desired field of view (FOV) and distance between the lens and the target preform. 16 mm was appropriate for this application.

Filters: (a) Neutral density filters for attenuation of intense furnace light. Different combinations of such filters were used at upper vs. lower positions, including various optical densities; (b) Red color filter to increase greyscale image contrast between glass edges and graphite background (i.e., the inner surface of the lower contact and lower protection tube); (c) Linear polarizing filter was used to remove unwanted reflections from glass surface that would interfere with measurement.

We claim:

1. An apparatus for heating and measuring a transparent cylindrical article during its manufacture, said apparatus comprising:

(A) a high temperature furnace comprising an upper and a lower contact, wherein each of the upper and the lower contact has an annular wall; and a heated interior positioned between the upper and lower contacts, wherein the annular wall of the lower contact has a lateral opening in communication with the heated interior and through which the transparent cylindrical article is visible at a vertical location where the heating is substantially complete and the article begins to cool;

(B) a digital camera having a lens affixed thereto and a sensing and digital recording device, wherein the lens receives an optical image of the transparent cylindrical article through the lateral opening of the lower annular wall, and directs the optical image to the sensing and digital recording device which converts the optical image to a digital image and records the digital image; and (C) a digital processor programmed with an algorithm which accesses and interprets the optical image from the sensing and digital recording device, and determines and reports a measurement of the cylindrical article, wherein the algorithm comprises the steps of:

(1) cropping the digital image to remove surrounding dark space and produce a smaller cropped digital image which includes only a bright field of view which was visible through the lateral opening of the furnace, wherein the smaller cropped digital image has a height and a width;

(2) producing a gradient filtered image from the cropped digital image using a standard deviation filter;

(3) performing multiple line scans and summing them together to form a grey level gradient spectrum having one or more left-sided peaks, one or more right-sided peaks and one or more minor background peaks, wherein the multiple line scans of the gradient spectrum are scanned within a scan area proximate to a vertical center of the gradient filtered image and extending horizontally across the full width of the gradient filtered image;

(4) identifying which of the one or more left-sided peaks and the one or more right-sided peaks in the grey level gradient spectrum represent true left- and right-side edges of the cylindrical article, by performing the following steps:

(a) on the grey level gradient spectrum, selecting a left-sided peak window area which encompasses the multiple left-sided peaks, and selecting a right-sided peak window area which encompasses the multiple right-sided peaks, leaving the minor background peaks outside each window area for separate analysis;
(b) establishing a baseline for peak detection which eliminates the minor background peaks from further analysis by:
(i) dynamically sampling a portion of the minor background peaks and calculating a noise floor level based on said dynamic sampling;
(ii) determining a baseline by adding to the noise floor level a threshold value;
(iii) thereafter, ignoring any peaks below said baseline;
(c) identifying a target left-sided peak and a target right-sided peak to provide numerical values for the positions of the true left- and right-sided edges of the cylindrical article, respectively, by:
(i) analyzing each of the multiple left-sided peaks which are higher than said baseline in the left-sided peak window area, selecting the target left-sided peak which is positioned farthest to the left in the left-sided peak window area and recording its position as a numerical value equal to the true left-sided edge of the cylindrical article;
(ii) analyzing each of the multiple right-sided peaks which are higher than said baseline in the right-sided peak window area, selecting the target right-sided peak which is positioned farthest to the right in the right-sided peak window area and recording its position as a numerical value equal to the true right-sided edge of the cylindrical article;
(5) calculating the outer diameter of the preform by taking the absolute value of the difference between the values of the true left- and right-sided edge of the cylindrical article; and
(6) reporting the outer diameter of the cylindrical article.

2. The apparatus of claim 1, wherein the transparent cylindrical article is an optical fiber preform comprising two or more layers of vitreous material.

3. The apparatus of claim 2, wherein the preform comprises a core layer having a refractive index and a cladding layer having a refractive index and surrounding the core layer, wherein the refractive index of the core layer is greater than the refractive index of the cladding layer.

4. The apparatus of claim 1, wherein the sensing and digital recording device comprises a charge-coupled device ("CCD") image sensor.

5. The apparatus of claim 1, wherein the measurement comprises a diameter of the cylindrical article.

6. The apparatus of claim 1, wherein the camera is enclosed in a fluid-tight, fluid-cooled housing having a portal, aligned with the opening of the furnace wall, for passage therethrough of the optical image of the cylindrical article.

7. The apparatus of claim 1, further comprising a reflector for directing the optical image received through the opening of the furnace wall and portal of the fluid-cooled housing to the lens of the camera.

8. The apparatus of claim 1, wherein the furnace is a jacketed fluid-cooled graphite furnace having a heated interior with upper and lower annular graphite contacts through which the cylindrical article passes while being heated, wherein the upper and lower contacts each have annular walls and are proximate opposite ends of the heated interior, wherein the lateral opening is in communication with the heated interior of the furnace, wherein the upper and lower contacts receive and conduct electric current therethrough for heating the heated interior of the graphite furnace with the cylindrical article therein, and wherein the furnace further includes a protection tube at the location where the heating is substantially complete and the article begins to cool.

9. A method for measuring a diameter of a transparent cylindrical article during manufacture of the transparent cylindrical article in a high temperature furnace, said method comprising:
(A) providing an apparatus comprising:
(i) a high temperature furnace comprising an upper and a lower contact, wherein each of the upper and the lower contact has an annular wall; and a heated interior positioned between the upper and lower contacts, wherein the annular wall of the lower contact has a lateral opening in communication with the heated interior and through which the transparent cylindrical article is visible at a vertical location where the heating is substantially complete and the article begins to cool;
(ii) a digital camera having a lens affixed thereto and a sensing and digital recording device, wherein the lens receives an optical image of the transparent cylindrical article through the lateral opening of the lower annular wall, and directs the optical image to the sensing and digital recording device which converts the optical image to a digital image and records the digital image; and
(iii) a digital processor programmed with an algorithm which accesses and interprets the optical image from the sensing and digital recording device, and determines and reports a measurement of the cylindrical article, wherein the algorithm comprises the steps of
(B) receiving an optical image of the cylindrical article emitted through the lateral opening of the digital camera;
(C) directing the optical image to the sensing and digital recording device;
(D) converting the optical image to a digital image, and recording the digital image, using the sensing and digital recording device; and
(E) interpreting the digital image and determining the diameter of the cylindrical article using the digital processor programmed with an algorithm, wherein the algorithm comprises the steps of:
(1) cropping the digital image to remove surrounding dark space and produce a smaller cropped digital image which includes only a bright field of view which was visible through the lateral opening of the furnace, wherein the smaller cropped digital image has a height and a width;
(2) producing a gradient filtered image from the cropped digital image using a standard deviation filter;
(3) performing multiple line scans and summing them together to form a grey level gradient spectrum having one or more left-sided peaks, one or more right-sided peaks and one or more minor background peaks, wherein the multiple line scans of the gradient spectrum are scanned within a scan area proximate to a vertical center of the gradient filtered image and extending horizontally across the full width of the gradient filtered image;
(4) identifying which of the one or more left-sided peaks and the one or more right-sided peaks in the grey level gradient spectrum represent true left- and right-side edges of the cylindrical article, by performing the following steps:
  (a) on the grey level gradient spectrum, selecting a left-sided peak window area which encompasses the multiple left-sided peaks, and selecting a right-sided peak window area which encompasses the multiple right-sided peaks, leaving the minor background peaks outside each window area for separate analysis;
  (b) establishing a baseline for peak detection which eliminates the minor background peaks from further analysis by:
    (i) dynamically sampling a portion of the minor background peaks and calculating a noise floor level based on said dynamic sampling;
    (ii) determining a baseline by adding to the noise floor level a threshold value;
    (iii) thereafter, ignoring any peaks below said baseline;
  (c) identifying a target left-sided peak and a target right-sided peak to provide numerical values for the positions of the true left- and right-sided edges of the cylindrical article, respectively, by:
    (i) analyzing each of the multiple left-sided peaks which are higher than said baseline in the left-sided peak window area, selecting the target left-sided peak which is positioned farthest to the left in the left-sided peak window area and recording its position as a numerical value equal to the true left-sided edge of the cylindrical article;
    (ii) analyzing each of the multiple right-sided peaks which are higher than said baseline in the right-sided peak window area, selecting the target right-sided peak which is positioned farthest to the right in the right-sided peak window area and recording its position as a numerical value equal to the true right-sided edge of the cylindrical article;
(5) calculating the outer diameter of the preform by taking the absolute value of the difference between the values of the true left- and right-sided edge of the cylindrical article; and
(6) reporting the outer diameter of the cylindrical article.

10. The method of claim 9, wherein the sensing and digital recording device is housed in the digital camera.

11. The method of claim 9, wherein the sensing and digital recording device is a charge-coupled device ("CCD") image sensor.

12. The method of claim 9, wherein the lateral opening of the furnace has a width less than the diameter of the cylindrical article.

13. The method of claim 9, wherein the directing step is performed using a reflector.

14. The method of claim 9, wherein, further to step (3), each gradient line scan is performed by setting a horizontal scan line position within the scan area of the gradient filtered image and sensing and recording the grey level of the image along the set horizontal scan line position.

15. The method of claim 9, wherein, further to step (3), wherein the multiple gradient line scans total 40 to 50 scans.

16. The method of claim 9, wherein, further to step (4)(a), wherein the left-sided peak window area is centered on a highest one of the multiple left-sided peaks and the right-sided peak window area is centered on a highest one of the multiple right-sided peaks.

17. The method of claim 9, further comprising determining a center position of the transparent cylindrical article by adding one half of the outer diameter to the value of the left-side edge.

18. The method of claim 9, wherein, further to step (4)(b)(ii), wherein the threshold value is equal to (a maximum peak height of the gray level gradient spectrum)−(the noise floor level)/(a predetermined factor).

19. The method of claim 9, wherein after performing step (1) cropping the digital image to produce a cropped digital image, said method further comprises calculating the average grey level in the cropped digital image and if the average grey level is below a predetermined threshold value, cease running algorithm.

20. The method of claim 9, wherein the threshold value is determined by calculating 0.5 times the average height of the portion of minor background peaks dynamically sampled.

21. A method for detecting a joint or defect within a transparent cylindrical article during manufacture of the transparent cylindrical article in a high temperature furnace; said method comprising:
  (A) providing an apparatus comprising:
    (i) a high temperature furnace comprising an upper and a lower contact, wherein each of the upper and the lower contact has an annular wall; and a heated interior positioned between the upper and lower contacts, wherein the annular wall of the lower contact has a lateral opening in communication with the heated interior and through which the transparent cylindrical article is visible at a vertical location where the heating is substantially complete and the article begins to cool;
    (ii) a digital camera having a lens affixed thereto and a sensing and digital recording device, wherein the lens receives an optical image of the transparent cylindrical article through the lateral opening of the lower annular wall, and directs the optical image to the sensing and digital recording device which converts the optical image to a digital image and records the digital image; and
    (iii) a digital processor programmed with an algorithm which accesses and interprets the optical image from the sensing and digital recording device, and determines and reports a measurement of the cylindrical article, wherein the algorithm comprises the steps of
  (B) receiving an optical image of the cylindrical article emitted through the lateral opening of the digital camera;
  (C) directing the optical image to the sensing and digital recording device;
  (D) converting the optical image to a digital image, and recording the digital image, using the sensing and digital recording device; and
  (E) interpreting the digital image and determining the presence of a joint or defect within the cylindrical article using the digital processor programmed with an algorithm, wherein the algorithm comprises the steps of:
    (1) cropping the digital image to remove surrounding dark space and produce a smaller cropped digital image which includes only a bright field of view which was visible through the lateral opening of the furnace, wherein the cropped digital image has a height and a width;
    (2) producing a gradient filtered image from the cropped digital image using a standard deviation filter;

(3) performing multiple line scans and summing them together to form a grey level gradient spectrum having one or more left-sided peaks, one or more right-sided peaks and one or more minor background peaks, wherein the multiple gradient lines are scanned within a scan area proximate to a vertical center of the gradient filtered image and extending horizontally across the full width of the gradient filtered image;

(4) identifying which of the one or more left-sided peaks and the one or more right-sided peaks in the grey level gradient spectrum represent true left- and right-side edges of the cylindrical article, by performing the following steps:

(a) on the grey level gradient spectrum, selecting a left-sided peak window area which encompasses the multiple left-sided peaks, and select selecting a right-sided peak window area which encompasses the multiple right-sided peaks, leaving the minor background peaks outside each window area for separate analysis;

(b) establishing a baseline for peak detection which eliminates the minor background peaks from further analysis by:
    (i) dynamically sampling a portion of the minor background peaks and calculating a noise floor level based on said dynamic sampling;
    (ii) determining a baseline by adding to the noise floor level a threshold value;
    (iii) thereafter, ignoring any peaks below said baseline;

(c) identifying a target left-sided peak and a target right-sided peak to provide numerical values for the positions of the true left- and right-sided edges of the cylindrical article, respectively, by
    (i) analyzing each of the multiple left-sided peaks which are higher than said baseline in the left-sided peak window area, selecting the target left-sided peak which is positioned farthest to the left in the left-sided peak window area and recording its position as a numerical value equal to the true left-sided edge of the cylindrical article;
    (ii) analyzing each of the multiple right-sided peaks which are higher than said baseline in the right-sided peak window area, selecting the target right-sided peak which is positioned farthest to the right in the right-sided peak window area and recording its position as a numerical value equal to the true right-sided edge of the cylindrical article; and (5) determining if there exists one or more intermediate peaks between the true left-sided peak and the true right-sided peaks.

22. The method of claim 21, wherein determining if there exists one or more intermediate peaks between the true left-sided peak and the true right-sided peak comprises: (1) selecting a central window of the grey level gradient spectrum between the true left-sided peak and the true right-sided peaks; (2) calculating an area of integration for the central window; and (3) determining if the area of integration exceeds a predetermined value.

* * * * *